United States Patent [19]

Matson et al.

[11] Patent Number: 5,238,671

[45] Date of Patent: * Aug. 24, 1993

[54] CHEMICAL REACTIONS IN REVERSE MICELLE SYSTEMS

[75] Inventors: Dean W. Matson, Kennewick; John L. Fulton, Richland; Richard D. Smith, Richland; Keith A. Consani, Richland, all of Wash.

[73] Assignee: Battelle Memorial Institute, Richland, Wash.

[*] Notice: The portion of the term of this patent subsequent to Jun. 12, 2007 has been disclaimed.

[21] Appl. No.: 274,558

[22] Filed: Nov. 22, 1988

Related U.S. Application Data

[63] Continuation of Ser. No. 125,842, Nov. 27, 1987, abandoned, and Ser. No. 152,256, Feb. 4, 1988, abandoned.

[51] Int. Cl.$^5$ .......................... C01B 7/00; B01J 13/00
[52] U.S. Cl. .................................. 423/397; 423/659; 252/309; 252/312
[58] Field of Search ................. 252/183.11, 308, 309, 252/312, 183.14; 524/546; 423/659, 397

[56] References Cited

PUBLICATIONS

R. W. Gale, et al., "Preparation of Monodispersed Nickel Boride Catalysts Using Reverse Micellar Systems" Preparation of Catalysts, Elsevier, Amsterdam (1983).
R. W. Gale, et al. Anal. Chem. (1987) 59, 1977-1979.
R. W. Gale, et al. J.A.C.S. (1987) 109, 920-1.
R. D. Smith, Separation Science and Technology, vol. 23 Oct. 1988.
Nagy et al. "Preparation of Monodispersed Nickel Boride Catalysts Using Reversed Micellar Systems", Preparation of Catalysts, Elsevier, Amsterdam (1983).

*Primary Examiner*—Prince Willis, Jr.
*Assistant Examiner*—John F. McNally
*Attorney, Agent, or Firm*—Marger, Johnson, McCollom & Stolowitz

[57] ABSTRACT

This invention is directed to conducting chemical reactions in reverse micelle or microemulsion systems comprising a substantially discontinuous phase including a polar fluid, typically an aqueous fluid, and a microemulsion promoter, typically a surfactant, for facilitating the formation of reverse micelles in the system. The system further includes a substantially continuous phase including a non-polar or low-polarity fluid material which is a gas under standard temperature and pressure and has a critical density, and which is generally a water-insoluble fluid in a near critical or supercritical state. Thus, the microemulsion system is maintained at a pressure and temperature such that the density of the non-polar or low-polarity fluid exceeds the critical density thereof. The method of carrying out chemical reactions generally comprises forming a first reverse micelle system including an aqueous fluid including reverse micelles in a water-insoluble fluid in the supercritical state. Then, a first reactant is introduced into the first reverse micelle system, and a chemical reaction is carried out with the first reactant to form a reaction product. In general, the first reactant can be incorporated into, and the product formed in, the reverse micelles. A second reactant can also be incorporated in the first reverse micelle system which is capable of reacting with the first reactant to form a product.

29 Claims, 1 Drawing Sheet excellent# CHEMICAL REACTIONS IN REVERSE MICELLE SYSTEMS

BACKGROUND OF THE INVENTION

This invention was made with United States Government support, and the Government has rights therein under Contract No. 2511006937 with the Department of the Army.

RELATED APPLICATIONS

This is a continuation of pending related applications U.S. Ser. No. 07/125,842, filed Nov. 27, 1987, and U.S. Ser. No. 07/152,256, filed Feb. 4, 1988, both now abandoned which are assigned to a common assignee, Battelle Memorial Institute.

SUMMARY OF THE INVENTION

This invention relates to the conduct of chemical reactions in reverse micelle or microemulsion systems comprising a substantially discontinuous phase including a polar fluid, typically an aqueous fluid, and a micelle or microemulsion promoter, typically a surfactant, for facilitating the formation of a reverse microemulsion or reverse micelles in the system. The system, which for purposes of this invention can be a reverse micelle or inverse microemulsion system, further includes a substantially continuous phase including a non-polar or low-polarity fluid material which is a gas under standard temperature and pressure and has a critical density, and which is generally a water-insoluble fluid in a near critical or supercritical state. A fluid is in a supercritical state when its temperature and pressure exceed its critical temperature and pressure. Thus, the system is maintained at a pressure and temperature such that the density of the non-polar or low-polarity fluid exceeds the critical density thereof. When the non-polar or low-polarity fluid is maintained in a near critical state, its preferred temperature is in a range from about 90° C. below the critical temperature thereof, up to the critical temperature thereof. These micelles formed are referred to as "reverse micelles" to distinguish them from the normal micelles of non-water-soluble fluids in aqueous liquids.

The method of carrying out chemical reactions generally comprises forming a first system including an aqueous fluid including reverse microemulsions or reverse micelles in a water-insoluble fluid in the near critical or supercritical state. Then, a first reactant is introduced into the first system, and a chemical reaction is carried out with the first reactant to form a reaction product. In general, the first reactant can be incorporated into, and the product formed in, the reverse microemulsions or reverse micelles. A second reactant can also be incorporated in the first system which is capable of reacting with the first reactant to form a product. The first and/or the second reactant can be capable of diffusing into or out of the reverse microemulsions or reverse micelles for conducting the subject chemical reactions. The reverse micelles or microemulsions typically comprise water and a surfactant.

The method of the present invention can also include the step of introducing a chemical catalyst, such as dispersed metallic particles or metallic compounds, or an energy source for initiating and/or driving the chemical reaction, such as radiation energy. Such chemical catalysts can include, for example, Pt, Pd, and Rh particles, or the borides of Ni, Co, and Fe, added to the system or formed in situ.

The first reactant can also be incorporated into the water-insoluble fluid for conducting the chemical reaction. Although the product formed can be soluble in either of the phases present, it is typically insoluble in water, in the supercritical fluid, or in the water and the supercritical fluid, respectively.

In a preferred method, the second reactant is incorporated into a second system typically comprising an aqueous fluid in a water-insoluble fluid in the supercritical or near critical state. The second system can then be added to the first system. For instance, a precipitation reaction may be provided employing solute species present in two distinct systems. In any case, the exchange of core materials occurs rapidly in the systems, ensuring complete mixing of the reactants. Two supercritical reverse micelle or microemulsion solutions can be prepared, each of which contains a water-soluble salt or other soluble reactant species dissolved in the aqueous cores of such solutions.

More specifically, although products which are soluble in the continuous or discontinuous phase may be formed by the method of this invention, this invention also relates to the formation of very fine particles by the reaction of a substance contained in the reverse microemulsion or micelles with a reactant added to the supercritical fluid which diffuses into the microemulsion or micelles and reacts with the substance to give a product insoluble in either water or supercritical fluid, or both.

The two solutions can comprise some combination of cations and anions which will produce an insoluble precipitate. The first and/or second reactant can comprise a water-soluble salt, such as sodium chloride, silver chloride, iron chloride, silver nitrate, barium hydroxide, calcium hydroxide, cadmium chloride, cadmium nitrate, cadmium chlorate, cadmium sulfide, cobalt chloride, cobalt sulfide, zinc sulfide, lead sulfide, and copper sulfide. It can also comprise an acidic material in aqueous solution such as an aqueous solution of sulfuric acid, a basic material in aqueous solution, and the water-insoluble fluid itself, or a reactant dissolved in the water-insoluble fluid such as an alkene or alkane. Further reactants may include a monomeric material or monomeric precursor material, such as tetraethoxysilane, dissolved in the water-insoluble or aqueous fluid, such as a hydrolysis/polymerization reaction catalyzed by an acidic or basic aqueous solution or other initiator in the reverse micelle system.

Still more specifically, it relates to a first reactant which is aqueous aluminum nitrate, a second reactant which is aqueous ammonia, and a reaction product which is aluminum hydroxide, and a particular method which comprises the production of submicron particles of aluminum hydroxide by forming reverse micelles of aluminum nitrate, water, and a surfactant, in supercritical propane and introducing ammonia into the propane phase.

The ability to form reverse micelles, or molecular assemblages consisting of surfactant shells with aqueous cores, in continuous nonpolar phases operated above their critical temperatures and pressures has recently been reported[1]. In this specification we describe the formation of inorganic, submicron particles in a supercritical hydrocarbon solution containing reverse micelles. A fine powder consisting of 0.5-micron-diameter aluminum hydroxide particles was precipitated from aqueous $Al(NO_3)_3$ solutions present in micelle cores by the diffusion of ammonia, a component in the binary supercritical fluid continuous phase, into the aqueous core. This work represents not only the first report of particle production using supercritical fluid micelles but is also the first example of a chemical reaction occurring within reverse micelles dispersed in a supercritical fluid.

Reverse micelles in liquids have been shown to offer a wide range of potential applications in the areas of chromatography, separations, and reaction processes[1-2-5]. In addition, chemical reactions involving species present in the reverse micelle cores have allowed the production of colloidal-size particles (3 to 10 nm) for use in catalytic and semiconductor applications[6-8]. Chemical processes utilizing systems in which reverse micelles exist in supercritical fluid regimes are expected to expand the scope of potential applications for micellar systems by utilizing the unique properties of supercritical fluids. These include such pressure-dependent variables as viscosity, density, and diffusion rate, as well as the ability to readily manipulate the P-T-phase behavior in the multicomponent micelle systems. Supercritical fluid reverse micelle phase stability is strongly dependent on the fluid pressure, and the amount of water that can be contained in the micelle core increases with the pressure applied to the fluid. At 100 bar and 103° C., the maximum water-to-AOT molar ratio for reverse micelles in a propane continuous phase is 4. This value increases to 12 at the same temperature and 300 bar[9].

BRIEF DESCRIPTION OF THE DRAWING

In the drawing: The single figure is a scanning electron micrograph of aluminum hydroxide particles produced by addition of ammonia to reverse micelles containing 0.1M Al($NO_3$)$_3$ in a supercritical propane solution at 100° C. and 200 bar.

DETAILED DESCRIPTION OF A PREFERRED EMBODIMENT

Figure 1:
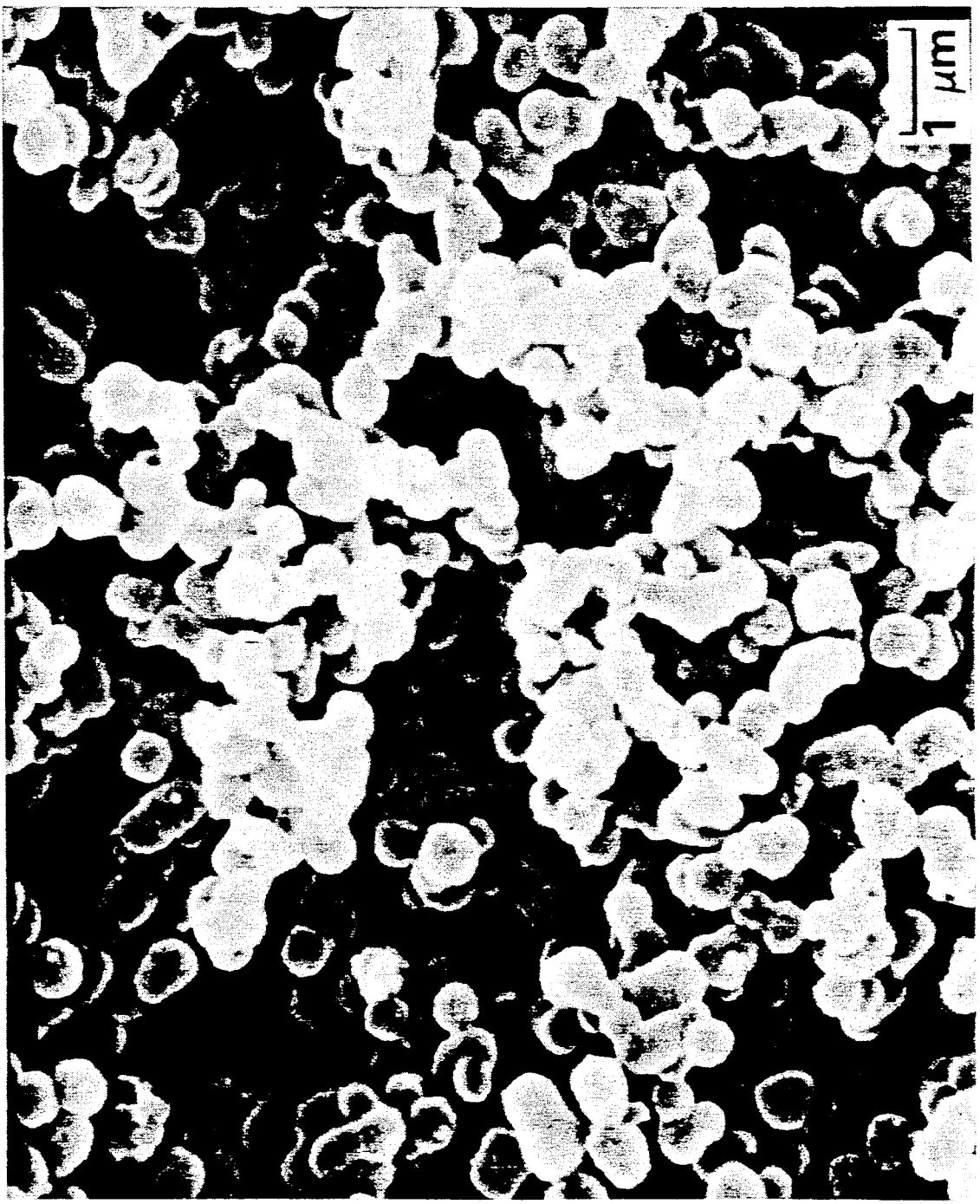

In this research aluminum hydroxide particles were prepared in a 25-ml high-pressure reaction vessel incorporating two 13-mm thick, 25-mm diameter sapphire windows through which the various steps in the reaction process could be observed. Before pressurizing with propane, the solid surfactant, sodium bis (2-ethylhexyl) sulfosuccinate (AOT), and the aqueous reaction solution, Al($NO_3$)$_3$·9$H_2O$ in water were charged into the vessel at a molar water to AOT ratio (W) of 5. In all experiments the AOT concentration was 50 mM. Three different Al(NO )$_3$ concentrations were used; 0.1M, 0.05M and 0.01M Al(NO )$_3$·9$H_2O$ in water. After reaching the desired reaction temperature, 100° C. in all cases, the system was pressurized to 200 bar with propane ($T_c$=96.8° C., $P_c$=42 atmospheres) by means of a high-pressure syringe pump. After several minutes of agitation with a magnetic stir bar, optically clear solutions were obtained, which contained the aqueous Al($NO_3$)$_3$ solution dispersed in the reverse micelle phase. In other experiments without the addition of AOT to the system, two phases, consisting of supercritical propane and the liquid aqueous phase, remained in the view cell under the same temperature and pressure conditions. Once temperature in the cell was stabilized, approximately 40 uL of dry ammonia was injected through a short length of small-bore (100-um-i.d.) tubing connected to a second syringe pump. Ammonia is known to exhibit considerable solubility in many supercritical hydrocarbons, including propane[10]. The ammonia was clearly evident (by the appearance of a milky plume which rapidly dissipated) as it was introduced into a reverse micelle solution consisting of pure water, AOT and supercritical propane. Addition of ammonia to a pure supercritical propane system produced a clear plume, suggesting that the milky plume produced in the micelle systems resulted from alteration of micelle phase behavior due to the locally high ammonia concentrations. Subsequent to addition of the ammonia, fluid in the view cell containing the 0.1M Al($NO_3$)$_3$ solution became turbid after approximately one minute but remained clear in the systems containing more dilute Al($NO_3$)$_3$ solutions. To collect and characterize particles formed in the supercritical fluid system, flow was established across a 0.5-um stainless steel frit mounted in-line to a flow restrictor through which the fluid in the cell was vented. Pressure was held constant in the cell during sample collection by the gradual addition of propane from a syringe pump.

Aluminum hydroxide particles precipitated by introduction of ammonia into a reverse micelle system containing 0.1M Al($NO_3$)$_3$ are shown in FIG. 1. Mean particle sizes are on the order of 0.5 um, with some evidence of "necking" between particles or minor agglomeration. It is not clear whether this behavior results from interactions in the solution prior to the particle deposition, or whether it is an artifact of collecting the sample on a porous frit where interactions between the high surface energy particles would be enhanced. The product particles collected from the system utilizing a 0.05M Al($NO_3$)$_3$ solution were significantly smaller (<0.1 um) and exhibited a much higher degree of agglomeration. No product was collected from the system utilizing the 0.01M Al($NO_3$)$_3$ solution, perhaps because any individual particles formed in that system were too small to be collected on the frit surface.

The particles shown in the figure are considerably larger than the reverse micelles present in the supercritical propane prior to introduction of the ammonia (5 to 10 nm). The phenomenon of particles far exceeding the sizes of micelles from which they were formed has also been observed during the formation of colloidal catalyst particles from reverse micelle phases in liquid systems[7,8]. This behavior has been attributed to the rapid exchange of contents between micelle cores, which could promote the coalescence of angstrom- or nanometer-size precipitated nuclei to form the much larger particles actually observed in the collected product.

The use of reaction processes in supercritical micelle solutions for powder production offers a number of potential advantages over existing technologies. The ability to manipulate the concentrations of reactants involved in the particle formation may allow the capability to finely control the particle size. Operation in the supercritical fluid regime may also allow high mass transfer rates of reactants to and across the micelle membranes, and should relax rate limitations when one of the reactants is a gas. Increased reaction rates are expected for diffusion limited reactions. High diffusion rates may reduce polydispersity of the particles produced by minimizing local concentration gradients due to the incomplete mixing. The pressure dependence of the phase and density behavior in supercritical fluid systems may also allow additional advantages to be gained in the area of particle separation from the continuous fluid phase in which it is produced.

Three examples of the chemical reactions of this invention are described below which were performed in reverse micelle systems in which propane was used as the water-insoluble fluid and aerosol-OT (AOT) was the surfactant. Each of the reactions described below was performed using system conditions of 100° C. and approximately 300 atm pressure, which is above the critical temperature and pressure of propane.

EXAMPLE 1

This example describes the reaction between reactants present in two distinct reverse micelle systems at supercritical conditions.

Two reverse micelle systems were made independently in high pressure viewcells. Both were prepared such that the final solution would have a final AOT concentration of approximately 50 mM. In one of the cells, 0.1M NaOH was added to make a water-to-surfactant ratio of approximately 11. The system was heated, pressurized, and stirred to form a clear, single-phase solution. In the other view cell, AOT was added and the system was pressurized and heated to the desired conditions. A quantity of 0.1M $Cu(NO_3)_2$ solution was added to the second cell from a high pressure hand-crank pump to make a reverse micelle solution having a water-to-surfactant ratio of approximately 13. The solution formed in the viewcell containing copper nitrate solution was one-phase and appeared slightly yellow in color.

When the supercritical fluid solutions had been prepared in both cells, a valve between them was opened. Pressure was vented slowly through a restrictor at the outlet of one of the cells so that a pressure differential existed between the cells and solution from one cell was transported into the other. Pressure was maintained in the upstream cell by adding propane from a high pressure syringe pump. After 25% of the solution in the downstream cell had been vented, the valves were closed and the solution was allowed to set for several minutes. The reaction resulting from the mixing of copper and hydroxide solutions was evidenced by the visible observation of fine particles (copper hydroxide) in the cell containing the mixed solutions.

EXAMPLE 2

This example describes the reaction between reactants present in a reverse micelle system at supercritical conditions and a water soluble reactant added to the system.

In a high pressure viewcell, AOT and 0.1M KCl solution were added in sufficient quantities to prepare a solution having an AOT concentration of approximately 75 mM and containing a water-to-surfactant ratio of approximately 3. The system was heated and pressurized to form a clear, single phase reverse micelle solution at supercritical conditions. A small amount of 0.1M $AgNO_3$ solution was added to the system using a high pressure hand-crank pump to raise the water-to-surfactant ratio of the system to between 5 and 7. After allowing the solution to set for several minutes, fine solid particles (silver chloride) were visually observed in the viewcell.

EXAMPLE 3

This example describes the reaction between reactants present in the supercritical fluid reverse micelle system and reactants dissolved in the continuous phase. The reaction was catalyzed by material present in the reverse micelle.

In a high pressure viewcell, AOT and 0.1M NaOH were added in appropriate quantities such that, when pressurized with supercritical propane, the resulting solution had an AOT concentration of approximately 50 mM and a water-to-surfactant ratio of 10. On achieving a clear solution at 100° C. and 300 atm, tetraethoxysilane (TEOS) was added to the cell at approximately ten times the water content using a high pressure hand-crank pump. TEOS is an alkane-soluble, water-insoluble silicate precursor to form interlinked Si-O-Si networks which are generated via hydrolysis of the TEOS monomer and subsequent polycondensation reactions. The reaction is catalyzed by the presence of either an acid or a base. This hydrolysis/condensation reaction was evidenced by visual observation of solid particles in the viewcell after approximately an hour. Fourier-transform infrared spectra taken on the supercritical fluid solution containing TEOS also provided evidence for an increasing concentration of Si-O-Si linkages in the system with time.

REFERENCES

1. Gale, R. W., J. L. Fulton, R. D. Smith. *J. Am. Chem. Soc.* 109. 1986. p. 920.
2. Sheu, E., K. E. Goklen, T. A. Hatton, S. H. Chen. *Biotechnol. Prog.* 2. 1986. p. 175.
3. *Reverse Micelles.* Eds. P. L. Luisi, B. E. Straub. Plenum Press, New York. 1984.
4. Luisi, P. L., Angew. *Chem., Int.* Ed. Engl. 24. 1985. p. 439.
5. Goklen, K. E., T. A. Hatton. *Biotechnol. Prog.* 1. 1985. p. 69.
6. Meyer, M., C. Wallberg, K. Curihara, J. H. Fendler. *J. Chem. Soc.,* Chem. Commun. 1984. p. 90.
7. Nagy, J. B., A. Gourgue, E. G. Derouane. *Preparation of Catalysts III.* Eds. G. Poncelet, P. Grange, P. A. Jacobs, P. A. Elsevier, Amsterdam. 1983. p. 193.
8. Lufimpadio, N., J. B. Nagy, E. G. Derouane. *Surfactants in Solution,* Vol. 3. Eds. K. L. Mittal, B. Lindman. Plenum, New York. 1984. p. 1483.
9. Gale, R. W., J. L. Fulton, R. D. Smith. *Anal. Chem.* 59. 1987. p. 1977.
10. Lentz, H., E. U. Franck. *Extraction with Supercritical Gases.* Eds. G. M. Schneider, E. Stahl, G. Wilke. Verlag Chemie, Weinheim. 1980. p. 83.

While we have described one example in detail, it will be obvious to those skilled in the art that various changes can be made. We, therefore, wish our invention to be limited solely by the scope of the appended claims.

We claim:

1. A method of carrying out chemical reactions which comprises forming a first reverse micelle or reverse microemulsion system comprising a first polar fluid, in a second fluid which is a gas at standard temperature and pressure and has a critical density, said second fluid being in a state in which the density of said second fluid exceeds said critical density, and including reverse micelles or reverse microemulsions;

introducing a first reactant to said first system; and carrying out a chemical reaction with said first reactant to form a reaction product.

2. The method of claim 1, which includes the step of incorporating said first reactant in the reverse micelles or reverse microemulsion.

3. The method of claim 1, which includes the step of forming said product in the reverse micelles or reverse microemulsion.

4. The method of claim 1, which includes the further step of adding a second reactant to said first system, said second reactant being capable of reacting with said first reactant to form a product.

5. The method of claim 4, wherein said second reactant is capable of diffusing into or out of said reverse micelles or reverse microemulsions for conducting said chemical reaction.

6. The method of claim 1, which includes the step of introducing an energy source into said first system for either one of initiating and driving said chemical reaction.

7. The method of claim 1, which includes the step of incorporating said first reactant into said water-insoluble fluid for conducting said chemical reaction.

8. The method of claim 7, which includes the step of incorporating a chemical catalyst into said system for initiating said chemical reaction.

9. The method of claim 1, wherein said first reactant is a water soluble salt.

10. The method of claim 1, wherein said product is insoluble in water, in the supercritical fluid, or in the water and the supercritical fluid, respectively.

11. The method of claim 1, wherein said reverse micelles comprise an aqueous fluid and a surfactant.

12. The method of claim 1, wherein said first reactant is aluminum nitrate, and said second reactant is ammonia, and said reaction product comprises submicron particles of aluminum hydroxide.

13. The method of claim 1, which includes the further step of incorporating a second reactant into a second system comprising a polar fluid in a non-polar or low-polarity fluid in the supercritical or near critical state; and adding said second system to said first system.

14. The method of claim 13, wherein said first reactant comprises one of a water-soluble salt, an acidic material and a basic material.

15. The method of claim 14, wherein said second reactant comprises one of a water-soluble salt, an acidic material and a basic material.

16. The method of claim 15, wherein said first reactant is sodium hydroxide, and said second reactant is copper nitrate.

17. The method of claim 13, wherein said polar phase comprises an aqueous fluid and a surfactant.

18. The method of claim 1, wherein said second reactant comprises said supercritical or near critical fluid.

19. A method of carrying out a chemical reaction, which comprises
forming a reverse micelle or reverse microemulsion system comprising an aqueous fluid in a water-insoluble fluid in the supercritical state;
incorporating a first reactant in said system; and
adding a second reactant to said system, said second reactant being water-soluble and being capable of diffusing into said reverse micelles or reverse microemulsion and carrying out a reaction with said first reactant to form a reaction product.

20. The method of claim 19, wherein said chemical reactions will form a product in said reverse micelles or reverse microemulsion.

21. A process for carrying out a chemical reaction, which comprises
forming a reverse micelle microemulsion system comprising a first substantially continuous phase including a low-polarity fluid material which is a gas under standard temperature and pressure and has a critical density, and a second substantially discontinuous phase including a polar fluid and a microemulsion or micelle promoter for facilitating the formation of reverse micelles or a reverse microemulsion in said first phase;
maintaining the system at a pressure and temperature such that the density of the low-polarity fluid exceeds the critical density thereof;
forming reverse micelles or a reverse microemulsion in said second phase;
introducing a first reactant into said microemulsion system; and
carrying out a chemical reaction with said first reactant to form a reaction product.

22. The process of claim 21, wherein said reaction is conducted at a temperature at least equal to the supercritical temperature of said fluid material.

23. The process of claim 21, wherein said promoter comprises a surfactant which is substantially soluble in said second phase.

24. The process of claim 21, wherein said fluid material is at least one lower alkane.

25. The process of claim 24, wherein said lower alkane is at least one of ethane, propane and butane.

26. The method of claim 1, wherein said second fluid comprises a non-polar fluid.

27. The method of claim 1, wherein said second fluid is in a supercritical state.

28. The method of claim 1, wherein said second fluid in said system comprises a supercritical fluid.

29. The method of claim 1, wherein said second fluid in said system comprises a liquid under pressure.

* * * * *